United States Patent [19]

Michaelis et al.

[11] 4,435,338
[45] Mar. 6, 1984

[54] DITHIOPHOSPHATES

[75] Inventors: Klaus-Peter Michaelis, Lindenfels; Rainer Schneider, Zwingenberg, both of Fed. Rep. of Germany

[73] Assignee: Ciba-Geigy Corporation, Ardsley, N.Y.

[21] Appl. No.: 303,748

[22] Filed: Sep. 21, 1981

[30] Foreign Application Priority Data

Sep. 29, 1980 [CH] Switzerland ............... 7277/80

[51] Int. Cl.³ .............................. C07F 9/17
[52] U.S. Cl. ................... 260/929; 252/46.6; 260/403; 260/930; 260/978; 544/214; 548/112
[58] Field of Search .................. 260/929, 930

[56] References Cited

U.S. PATENT DOCUMENTS 2,921,086 1/1960 McCall et al. ............ 260/929 X
3,197,405 7/1965 Le Suer .................... 260/928

FOREIGN PATENT DOCUMENTS 49222 4/1982 European Pat. Off. .

Primary Examiner—Anton H. Sutto
Attorney, Agent, or Firm—Luther A. R. Hall

[57] ABSTRACT

The compounds according to the invention correspond to the formula I

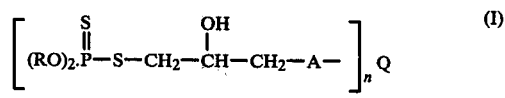

in which R is a hydrocarbon radical, A is one of the groups —O.CO—, —O— or

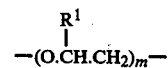

(in which m is 0-30) and Q, depending on the definition of A, is a hydrocarbon radical, a P-containing radical, an N-heterocyclic group or a radical containing N-heterocyclic groups.

The compounds according to the invention also include those which are formed by an addition reaction of an O,O-dialkyl dithiophosphate with an epoxidised soybean oil.

The compounds according to the invention are very useful as lubricant additives.

4 Claims, No Drawings

DITHIOPHOSPHATES

The invention relates to novel dithiophosphates, their preparation and their use in lubricating oils.

Dithiophosphates and their use as lubricant additives have already been described; in the preparation of these compounds, a monoepoxide is introduced into the molecule of the adduct by an addition reaction. Such products are described, for example, in German Offenlegungsschrift No. 2,802,756.

The invention relates to compounds of the formula I

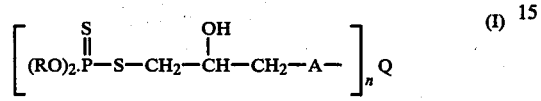

in which n is 2, 3 or 4 and is the valency of Q, R is an aromatic and/or aliphatic straight-chain or branched, saturated or unsaturated, $C_1$-$C_{22}$-hydrocarbon radical which can be substituted by —OH or halogen or be interrupted by —O— or —S—, and A is one of the groups —O.CO—, —O— or $$-(O.\overset{R^1}{\underset{|}{C}H.CH_2})_m-$$

in which m is a number from 0 to 30 and $R^1$ is —H or —CH₃, and in which (a) if A is —O.CO— or —O—, the radical Q is a divalent, trivalent or tetravalent aromatic or aromatic-aliphatic or aliphatic hydrocarbon radical, which has 6 to 11 C atoms, and can be substituted by —OH, halogen, -S-methyl or -O-methyl and be interrupted by —S—, —O— or —NH— bridges, and in the specific case where A is —O—, the radial Q can also be

(b) if A is $$-(O.\overset{R^1}{\underset{|}{C}H.CH_2})_m-,$$

the radical Q is a divalent 5-membered or 6-membered heterocyclic group (E) which contains 2 N atoms in the ring, or is a divalent, aliphatic radical containing 2 heterocyclic groups (E), the bonding to A being via N-heretoatoms, or is the trivalent group

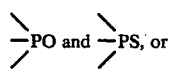

or the trivalent group

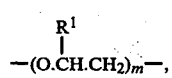

or is a divalent group of the formula

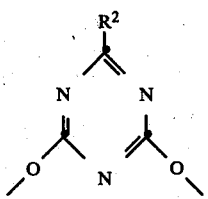

in which $R^2$ is —O.CH₃,

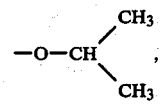

—S.CH₃, —NH.CH₃, —S.CH₂COO—i-octyl,

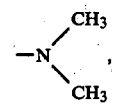

$C_1$-$C_{22}$-alkyl or phenyl.

Preferred compounds according to the invention are those in which, in formula I, A is the group $$-(O.\overset{R^1}{\underset{|}{C}H.CH_2})_m-$$

and Q is a heterocyclic group (E) from the series comprising the hydantoin, uracil, dihydrouracil, barbituric acid and ethyleneurea radical or is a divalent aliphatic radical, containing 2 identical heterocyclic groups (E) of this series, the groups (E) being substituted or unsubstituted, and the bonding between A and Q being via N-heteroatoms.

Further preferred compounds according to the invention are substances of the formula I, in which A is the group —O.CO— and Q is a group from the series comprising

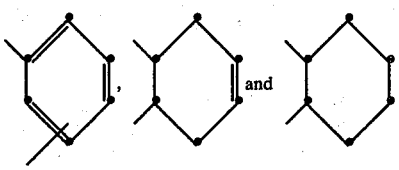

or A is the group —O— and Q is one of the radicals

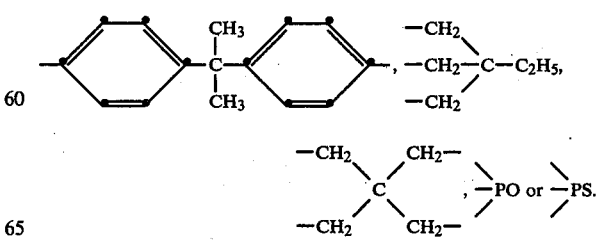

An aliphatic hydrocarbon radical R can be linear or, in particular, branched alkyl, which can be interrupted by O or S atoms, or cycloalkyl or cycloalkylalkyl which can be substituted by 1 or 2 alkyl groups, preferably having 1 to 12 C atoms. An aromatic hydrocarbon radical R can be aryl or aralkyl which can be substituted by 1 or 2 alkyl groups. Alkyl preferably has 1 to 30, especially 1 to 24, and more especially 1 to 18 C atoms, and cycloalkyl has 5 to 8 ring carbon atoms and is preferably cyclohexyl. Aryl is preferably phenyl and aralkyl is preferably benzyl, and the cycloalkyl, phenyl or benzyl radical is preferably substituted by 1 or 2 alkyl groups.

Examples of R are methyl, ethyl, propyl, butyl, i-butyl, t-butyl, pentyl, hexyl, 2-methylpentyl, heptyl, octyl, 2-ethylhexyl, nonyl, i-nonyl, decyl, undecyl, dodecyl, 2-ethyldecyl, t-dodecyl, tetradecyl, octadecyl, i-octadecyl, eicosyl, docosyl, tetracosyl, methoxyethyl, methoxy-n-propyl, octoxyethyl, octylthioethyl, cyclopentyl, methylcyclopentyl, ethylcyclopentylmethyl, cyclohexylmethyl, methylcyclohexyl, p-nonylcyclohexyl, cyclododecyl, methylphenyl, ethylphenyl, t-butylphenyl, dimethylphenyl, hexylphenyl, i-octylphenyl, nonylphenyl, dinonylphenyl, dodecylphenyl, methoxyphenyl, methylbenzyl, nonylbenzyl and dodecylbenzyl.

R can also be the radical of an industrial alcohol or alcohol mixture. These alcohols are in general prepared by the Ziegler process from aluminum, hydrogen and ethylene, followed by hydroxylation, and are mostly mixtures of different branched alcohols. They are commercially available, examples being Guerbet alcohols and Alfols (manufactured by Condea), Dobanols (manufactured by Shell) and Oxanols (manufactured by Ruhrchemie).

Preferably, R in formula I is $C_3$-$C_8$-alkyl, especially I-propyl or i-octyl.

The range of groups Q in formula I follows directly from the discussion, given later, of the polyepoxide compounds used in the process of preparation, so that further discussion of Q at the present stage is superfluous.

A preferred compound of the formula I has the structure

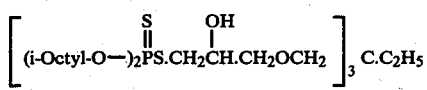

The invention also relates to a process for the preparation of compounds of the formula I, which comprises subjecting an O,O-dialkyl dithiophosphate of the formula II

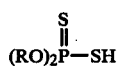 (II)

and an epoxy compound of the formula III

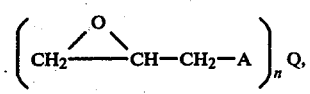 (III)

to an addition reaction at 50° to 100° C., if appropriate in an inert organic solvent, the reactants being employed in a ratio which provides about n mols of the compound of the formula II per mol of the compound of the formula III, and then removing any solvent used.

Preferably, the addition reaction is carried out in an inert organic solvent.

The dithiophosphoric acid esters of the formula II are known substances and can be prepared in a simple manner by reacting $P_2S_5$ with the corresponding alcohols ROH (cf., for example, German Offenlegungsschrift No. 2,802,756).

Suitable epoxide compounds of the formula III are, inter alia, virtually all commercially available difunctional, trifunctional or tetrafunctional epoxide compounds. These include, in particular, ether-like epoxy resins which are prepared by reacting epichlorohydrin with alcohols, for example tris-methylolpropane and pentaerythritol, or with phenols, for example bisphenol-A, bisphenol-F or diphenol, or with the corresponding nuclear-hydrogenated phenols.

Epoxide compounds of the formula III having ester-like character, i.e. in which A is the group —O.CO—, can be either reaction products of aliphatic and aromatic acids with epichlorohydrin, or the products of trans-esterifying esters of aliphatic and aromatic acids with glycidol. Preferred compounds of this type are the diglycidyl compounds of the phthalic acids, tetrahydro-o-phthalic acid and hexahydro-o-phthalic acid. Another epoxide compound of the formula III, having ester-like character, is triglycidyl phosphate. This known substance is mentioned, for example, in C.A., Vol. 83 (1975), 99, 121 p, U.S. Pat. No. 2,856,369, U.S. Pat. No. 2,826,592 and Plaste Kautschuk (9) 11 (1964), 515 (A. Wende et al.).

For the preparation of the products of the formula I, in which A is

the epoxide compounds of the formula III which are employed are, in particular, the known substances which contain 5-membered or 6-membered heterocyclic groups (E) with 2 N atoms in the ring. The compound may contain one or 2 such heterocyclic groups (E). In connection with these compounds, reference may be made to the following U.S. Pat. Nos. 3,429,833, 3,449,353, 3,592,823, 3,542,803, 3,503,979, 3,496,180, 3,562,275, 3,562,274, 3,772,326, 3,629,263, 3,161,594, 3,631,221, 3,679,681, 4,038,277, 3,821,243, 3,907,719 and 3,975,397. Furthermore, in this type of case, triglycidyl isocyanurate and triglycidyl cyanurate can also be employed as compounds of the formula III. In this context, reference may be made to a publication by M. Budnowski in Kunststoffe 55 (1965), 641–647.

All these epoxide compounds are statistical mixtures of monomeric and oligomeric compounds.

In cases in which A is —O.CO— or —O— the compounds of the formula I can also be prepared as follows. An O,O-dialkyl dithiophosphate of the formula II is reacted with glycidol. The adduct obtained, which contains one terminal OH group and one lateral OH group on the propylene group formed, is subsequently subjected to a condensation reaction with an acid derivative, such as a halide, anhydride or ester. The amount of the acid derivative is chosen so that virtually only the more active terminal OH group reacts.

The invention also relates to a product obtained by addition reaction of an O,O-dialkyl dithiophosphate, preferably O,O-di-2-ethylhexyl dithiophosphate, with an epoxidised soybean oil at 50° to 100° C., and to the preparation of this product.

The latter is carried out by subjecting an O,O-dialkyl dithiophosphate to an addition reaction with an epoxidised soybean oil, if appropriate in an inert organic solvent, using the reactants in such a ratio that the —SH groups and the epoxide groups are present in approximately stoichiometric amounts, and employing a reaction temperature of 50° to 100° C.

The compounds according to the invention, of the formula I, and the P-containing products according to the invention, based on epoxidised soybean oil and obtained by an addition reaction, are effective, even in very small amounts, as extreme-pressure additives in lubricants. Thus, mineral lubricating oils and synthetic lubricating oils, as well as mixtures thereof, which contain 0.01 to 5% by weight, preferably 0.05 to 3% by weight, based on the lubricant, of one of these compounds according to the invention exhibit excellent extreme-pressure lubricating properties, which manifest themselves in greatly reduced wear of the components to be lubricated (EP/AW additives). The relevant lubricants are familiar to those skilled in the art and are described, for example, in the "Schmiermittel Taschenbuch" ("Lubricant Handbook") (Hüthig Verlag, Heidelberg, 1974).

Accordingly, the invention also relates to compositions of matter which comprise a mineral lubricating oil and/or synthetic lubricating oil and a compound of the formula I according to claim 1, or a plurality of such compounds, and to the use of the compounds of the formula I as lubricant additives.

The invention yet further relates to compositions of matter comprising a mineral lubricating oil and/or synthetic lubricating oil and a product according to the invention, obtained by addition reaction of an O,O-dialkyl dithiophosphate with an epoxidised soybean oil at 50° to 100° C., and to the use of this adduct as a lubricant additive.

The lubricating oil can moreover contain other additives which are introduced in order to improve its properties, such as antioxidants, metal passivators, rust inhibitors, viscosity index improvers/pour point depressants, dispersants/detergents and other extreme-pressure/anti-wear additives.

Examples of antioxidants are:

(a) Alkylated and non-alkylated aromatic amines and mixtures of these, for example dioctylphenylamine, mono-t-octylphenyl-α-naphthylamines and -β-naphthylamines, phenothiazine, dioctylphenothiazine, phenyl-α-naphthylamine and N,N'-di-sec-butyl-p-phenyldiamine.

(b) Sterically hindered phenols, for example 2,6-di-tert-butyl-p-cresol, 4,4'-bis-(2,6-diisopropylphenyl), 2,4,6-triisopropylphenol, 2,2'-thio-bis-(4-methyl-6-tert-butyl-phenol) and 4,4'-methylene-bis-(2,6-di-t-butyl-phenol).

(c) Alkyl phosphites, aryl phosphites or alkyl aryl phosphites, for example trinonyl phosphite, triphenyl phosphite and diphenyl decyl phosphite.

(d) Esters of thiodipropionic acid or thiodiacetic acid, for example dilauryl thiodipropionate or dioctyl thiodiacetate.

(e) Salts of carbamic acids and dithiophosphoric acids, for example antimony diamyldithiocarbamate and zinc diamyldithiophosphate.

(f) Metal salts and metal complexes of organic chelating agents, for example copper bis-trifluoroacetylacetonate, copper phthalocyanines and the tributyl ester of the monosodium salt of ethylenediaminetetraacetic acid.

(g) Free radical antioxidants, for example nitroxides.

(d) Combinations of two or more antioxidants from the above, for example an alkylated amine and a sterically hindered phenol.

Examples of metal passivators are:

(a) For copper, for example, 1,2,4-triazoles, benzotriazole, tetrahydrobenzotriazole, 2,5-dimercaptothiadiazole, salicylidene-propylenediamine and salts of salicylaminoguanidine.

(b) For magnesium, for example, pyridylamines.

(c) For lead, for example, sebacic acid, quinizarine and propyl gallate.

(d) Combinations of two or more of the above additives.

Examples of rust inhibitors are:

(a) Organic acids, their esters, metal salts and anhydrides, e.g. N-oleoyl-sarcosine, sorbitan monooleate, lead naphthenate and dodecenylsuccinic anhydride.

(b) Nitrogen-containing compounds, e.g.:

I. Primary, secondary or tertiary aliphatic or cycloaliphatic amines and amine salts of organic and inorganic acids, for example oil-soluble alkylammonium carboxylates.

II. Heterocyclic compounds, for example imidazolines and oxazolines.

(c) Phosphorus-containing compounds, e.g. amine salts of partial esters of phosphoric acid.

(d) Sulfur-containing compounds, e.g. barium dinonylnaphthalenesulfonates and calcium petrolenesulfonates.

(e) Combinations of two or more of the above additives.

Examples of viscosity index improvers/pour point depressants are polymethacrylates, polybutenes, olefin copolymers, polyvinylpyrrolidone and polymethacrylate copolymers.

Examples of dispersants/detergents are metal sulfonates (the metal being Ca, Ba or Mg) and metal phenates, as well as polybutenyl-succinimides.

Examples of extreme-pressure/anti-wear additives are materials containing sulfur and/or phosphorus and/or halogen, e.g. zinc dialkyl-phosphorodithioates, tritolyl phosphate and chlorinated paraffin.

The compounds according to the invention, of the formula I, and the P-containing products according to the invention, based on epoxidised soybean oil and obtained by an addition reaction, are also used as acaricides and insecticides.

The examples which follow illustrate the invention.

It is to be assumed that the reaction products in the examples which follow are statistical mixtures of monomeric and oligomeric compounds. The composition of the mixtures essentially depends on the reaction conditions and on the ratio in which the reactants are present in the mixture. The products are pale brown and viscous, and are obtained in virtually quantitative yield. In all the examples, the reaction has evidently gone to completion, since the SH content and epoxide content are virtually zero. In every case, the substances were identified as O,O-dialkyl S-alkyl dithiophosphates by phosphorus-NMR.

EXAMPLE 1

$$[(\text{i-Oct.-O})_2\overset{S}{\overset{\|}{P}}-S-CH_2-\overset{OH}{\overset{|}{C}H}CH_2OCH_2]_3CC_2H_5$$

A solution of 141.6 g (73% SH) of O,O-di-2-ethylhexyl dithiophosphate in 200 ml of toluene is treated with 39.2 g of an epoxy compound of the formula $$(\overset{O}{\overset{/\ \backslash}{CH_2\text{——}CH}}CH_2OCH_2)_3CC_2H_5$$

in the course of 1.5 hours at 60° C., with stirring, and stirring is then continued for 2 hours at 80°–90° C. The solvent is distilled in vacuo from the adduct obtained.
$n_D^{20}$: 1.4991.

EXAMPLE 2

$$\left[(\text{i-Oct.-O})_2\overset{S}{\overset{\|}{P}}SCH_2\overset{OH}{\overset{|}{C}H}CH_2OCH_2]_2C[CH_2OCH_2\overset{OH}{\overset{|}{C}H}CH_2S\overset{S}{\overset{\|}{P}}(O-\text{i-Oct.})_2\right]_2$$

A solution of 70.8 g (75% SH) of O,O-di-2-ethylhexyl dithiophosphate in 100 ml of toluene is treated with 20 g of an epoxy compound of the formula $$(\overset{O}{\overset{/\ \backslash}{CH_2\text{——}CH}}CH_2OCH_2)_2C(CH_2OCH_2\overset{O}{\overset{/\ \backslash}{CH\text{——}CH_2}})_2$$

in the course of 1 hour at 60° C., with stirring, and the mixture is then stirred for 2 hours at 80°–90° C. After determination of the SH content and epoxide content, the solvent is distilled in vacuo from the adduct obtained.
$n_D^{20}$: 1.4989.

EXAMPLE 3

$$\left[\left(\overset{CH_3}{\underset{CH_3}{\diagdown}}CH-O\right)_2\overset{S}{\overset{\|}{P}}SCH_2\overset{OH}{\overset{|}{C}H}CH_2OCH_2]_2C[CH_2OCH_2\overset{OH}{\overset{|}{C}H}CH_2S\overset{S}{\overset{\|}{P}}\left(O-CH\overset{CH_3}{\underset{CH_3}{\diagup}}\right)_2\right]_2$$

A solution of 46.3 g (0.2 mol) of ammonium O,O-diisopropyl dithiophosphate in 100 ml of toluene is treated with 40 g of an epoxy compound of the formula $$(\overset{O}{\overset{/\ \backslash}{CH_2\text{——}CH}}CH_2OCH_2)_2C(CH_2OCH_2\overset{O}{\overset{/\ \backslash}{CH\text{——}CH_2}})_2$$

in the course of 1 hour at 60° C., with stirring, and the mixture is then stirred for 2 hours at 80°–90° C. After determination of the SH content and epoxide content, the solvent is distilled in vacuo from the adduct obtained. The resulting product is so viscous that it is not possible to determine its refractive index.

EXAMPLE 4

$$\left[(\text{i-Oct.-O})_2\overset{S}{\overset{\|}{P}}SCH_2\overset{OH}{\overset{|}{C}H}CH_2O-\!\!\left\langle\!\!\bigcirc\!\!\right\rangle\!\!-\right]_2\!\!-\overset{CH_3}{\underset{CH_3}{\overset{|}{\underset{|}{C}}}}-$$

A solution of 66.4 g (80% SH) of O,O-di-2-ethylhexyl dithiophosphate in 100 ml of toluene is treated with 25.5 g of an epoxide compound of the formula $$(\overset{O}{\overset{/\ \backslash}{CH_2\text{——}CH}}CH_2O-\!\!\left\langle\!\!\bigcirc\!\!\right\rangle\!\!-)_2-\overset{CH_3}{\underset{CH_3}{\overset{|}{\underset{|}{C}}}}$$

in the course of 1 hour at 60° C., with stirring, and the mixture is then stirred for 2 hours at 80°–90° C. After determination of the SH content and epoxide content, the solvent is distilled in vacuo from the adduct obtained.
$n_D^{20}$: 1.5228.

EXAMPLE 5

$$\begin{array}{c}CH_3\\CH_3\end{array}\!\!\underset{GN}{\overset{\phantom{X}}{\diagup}}\!\!\underset{\underset{O}{\overset{\|}{Y}}}{\overset{O}{\diagdown\!\!\diagup}}\!\!\underset{NG}{\phantom{X}}\quad G=-CH_2\overset{OH}{\overset{|}{C}H}CH_2S\overset{S}{\overset{\|}{P}}(O-\text{i-Oct.})_2$$

A solution of 66.4 g (80% SH) of O,O-di-2-ethylhexyl dithiophosphate in 100 ml of toluene is treated with 18 g of an epoxide compound of the formula $$\begin{array}{c}CH_3\\CH_3\end{array}\!\!\underset{G^1N}{\overset{\phantom{X}}{\diagup}}\!\!\underset{\underset{O}{\overset{\|}{Y}}}{\overset{O}{\diagdown\!\!\diagup}}\!\!\underset{NG^1}{\phantom{X}}\quad G^1=-CH_2\overset{O}{\overset{/\ \backslash}{CH\text{——}CH_2}}$$

in the course of about 1 hour at 60° C., with stirring, and the mixture is then stirred for 0.5 hour at 80°–90° C. After determination of the SH content and epoxide content, the solvent is distilled in vacuo from the adduct obtained.

The substance obtained is very viscous. It is not possible to determine its refractive index.

EXAMPLE 6

$$\text{CH}_3\text{-}\underset{\underset{G^2N\quad NG^2}{\diagdown\diagup}}{\overset{\text{CH}_3}{\text{C}}}\text{-}\overset{\text{O}}{\underset{\|}{\text{C}}}$$
$$\underset{\text{O}}{\|}$$

$$G^2 = -\text{CH}_2\overset{\text{CH}_3}{\underset{|}{\text{CH}}}\text{OCH}_2\overset{\text{OH}}{\underset{|}{\text{CH}}}\text{CH}_2\overset{\text{S}}{\underset{\|}{\text{SP}}}\left(\text{O}-\text{CH}\diagup\overset{\text{CH}_3}{\diagdown\text{CH}_3}\right)_2$$

A solution of 46.6 g (0.2 mol) of ammonium O,O-diisopropyl dithiophosphate in 100 ml of toluene is treated with 53.4 g of an epoxide compound of the formula $$\text{CH}_3\text{-}\underset{\underset{G^3N\quad NG^3}{\diagdown\diagup}}{\overset{\text{CH}_3}{\text{C}}}\text{-}\overset{\text{O}}{\underset{\|}{\text{C}}} \quad G^3 = -\text{CH}_2\overset{\text{CH}_3}{\underset{|}{\text{CH}}}\text{OCH}_2\text{CH}\overset{\text{O}}{\diagup\diagdown}\text{CH}_2$$
$$\underset{\text{O}}{\|}$$

in the course of 1 hour at 60° C., with stirring, and the mixture is then stirred for 2 hours at 80°–90° C. After determination of the SH content and epoxide content, the solvent is distilled in vacuo from the adduct obtained.

$h_D^{20}$: 1.5124.

EXAMPLE 7

$$\left[\text{CH}_3\diagdown\underset{\underset{GN\quad N\quad CH_2}{\diagdown\diagup}}{\overset{\text{CH}_3}{\text{C}}}\diagup\overset{\text{O}}{\underset{\|}{\text{C}}}\text{CHOG}\right]_2$$
$$\underset{\text{O}}{\|}$$

$$G = -\text{CH}_2\overset{\text{OH}}{\underset{|}{\text{CH}}}\text{CH}_2\overset{\text{S}}{\underset{\|}{\text{SP}}}(\text{O}-i\text{-Oct.})_2$$

A solution of 53.1 g (0.15 mol) of O,O-di-2-ethylhexyl dithiophosphate in 100 ml of toluene is treated with 24 g of an epoxide compound of the formula $$\left[\text{CH}_3\diagdown\underset{\underset{G^1N\quad N\quad CH_2}{\diagdown\diagup}}{\overset{\text{CH}_3}{\text{C}}}\diagup\overset{\text{O}}{\underset{\|}{\text{C}}}\text{CHOG}^1\right]_2 \quad G^1 = -\text{CH}_2\text{CH}\overset{\text{O}}{\diagup\diagdown}\text{CH}_2$$
$$\underset{\text{O}}{\|}$$

in the course of 1 hour at 60° C., with stirring, and the mixture is then stirred for 1 hour at 80°–90° C. After determination of the SH content and epoxide content, the solvent is distilled in vacuo from the adduct obtained.

$n_D^{20}$: 1.5086.

EXAMPLE 8

The reaction product of O,O-di-2-ethylhexyl dithiophosphate with epoxidised soybean oil.

A solution of 35.4 g (0.1 mol) of O,O-di-2-ethylhexyl dithiophosphate in 100 ml of toluene is treated with 26.3 g of epoxidised soybean oil in the course of 1 hour at 60° C., with stirring, and the mixture is then stirred for 1 hour at 80°–90° C. After determination of the SH content and epoxide content, the solvent is distilled in vacuo from the adduct obtained.

$n_D^{20}$: 1.4960.

EXAMPLE 9

$$[(^i\text{OcO})_2\overset{\text{S}}{\underset{\|}{\text{P}}}\text{SCH}_2\overset{\text{OH}}{\underset{|}{\text{CH}}}\text{CH}_2\text{O}]_3\text{P}=\text{O}$$

A solution of 147.7 g (73% SH) of O,O-di-2-ethylhexyl dithiophosphate in 500 ml of toluene was treated with 31.9 g of $$(\text{CH}_2\overset{\text{O}}{\diagup\diagdown}\text{CHCH}_2\text{O})_3\text{P}=\text{O}$$

in the course of 1 hour at 60° C., with stirring, and the mixture was then stirred for 2 hours at 80°–90° C. After determination of the SH content and epoxide content, the solvent was distilled in vacuo from the adduct obtained.

$n_D^{20}$: 1.4992.

USE EXAMPLES

Using the Shell four ball machine, the following values were determined in accordance with DIN 51,350: (tentative method IP 239/69, extreme-pressure and wear lubricant test for oils and greases, four ball machine).

(1) I.S.L.=initial seizure load: this is the load at which the oil film collapses within 10 seconds' duration of load.

(2) W.L.=weld load. This is the load under which the four balls weld together within 10 seconds.

(3) W.S.D.=wear scar diameter in mm: this is the mean wear diameter observed under a load of 70 kg or 40 kg applied for 1 hour.

The base oil used is an additive-free mineral lubricating oil.

The results of these experiments are summarised in the table. The oil mixtures containing the compounds according to the invention are distinguished by good extreme-pressure and anti-wear properties (ISL, WL and WSD). They are stable to hydrolysis and do not cause any corrosion of iron.

The volatilisation of the compounds according to the invention from the oil mixtures is slight.

| Lubricant additive | | ISL | WL | WSD |
|---|---|---|---|---|
| Type | Concentration in % by weight | (kg) | (kg) | (kg) |
| according to Example 1 | 1 | 110 | 200 | 0 |
| according to Example 2 | 1 | 90 | 210 | 0.4 |
| according to Example 3 | 1 | 100 | 210 | 0.4 |

| Lubricant additive | | ISL (kg) | WL (kg) | WSD (kg) |
|---|---|---|---|---|
| Type | Concentration in % by weight | | | |
| according to Example 4 | 1 | 90 | 200 | 0.4 |
| according to Example 5 | 1 | 110 | 230 | 0.4 |
| according to Example 6 | 1 | 80 | 220 | 0.4 |
| according to Example 7 | 1 | — | 180 | 0.3 |
| according to Example 8 | 1 | 80 | 210 | 0.5 |

What is claimed:

1. A compound of the formula

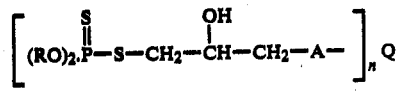
(I)

in which n is 2, 3 or 4 and is the valency of Q,

R is a hydrocarbon radical having 1 to 22 carbon atoms, or said radical having an —O— or —S— group in the chain, or said radical substituted by hydroxy or by halogen, A is the group —OCO— and Q is a group

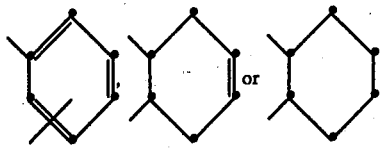

or A is the group —O— and Q is one of the radicals

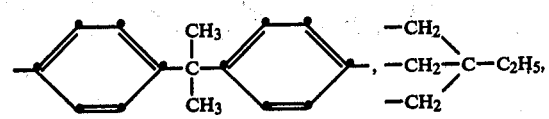

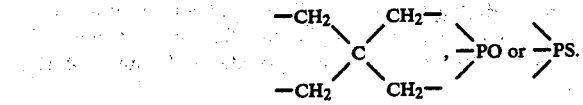

2. A compound according to claim 1, of the formula I, in which R is $C_3$-$C_8$-alkyl.

3. A compound according to claim 2 wherein R is isopropyl or isooctyl.

4. A compound according to claim 1, of the formula I, which has the structure

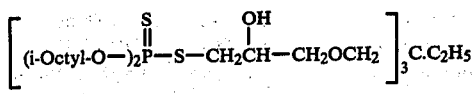

* * * * *